(12) United States Patent
Roth-Walter et al.

(10) Patent No.: US 10,914,744 B2
(45) Date of Patent: Feb. 9, 2021

(54) METHOD AND MEANS FOR DIAGNOSING AND TREATING ALLERGY

(71) Applicant: BIOMEDICAL INTERNATIONAL R+D GMBH, Vienna (AT)

(72) Inventors: Franziska Roth-Walter, Vienna (AT); Erika Jensen-Jarolim, Vienna (AT); Cristina Gomez-Casado, Getafe (ES); Araceli Diaz Perales, Madrid (ES); Luis Fernandez Pacios, Madrid (ES); Josef Singer, Kleinbaumgarten (AT)

(73) Assignee: BIOMEDICAL INTERNATIONAL R+D GMBH, Vienna (AT)

( * ) Notice: Subject to any disclaimer, the term of this patent is extended or adjusted under 35 U.S.C. 154(b) by 750 days.

(21) Appl. No.: 15/111,162

(22) PCT Filed: Jan. 7, 2015

(86) PCT No.: PCT/EP2015/050126
§ 371 (c)(1),
(2) Date: Jul. 12, 2016

(87) PCT Pub. No.: WO2015/104270
PCT Pub. Date: Jul. 16, 2015

(65) Prior Publication Data
US 2016/0334418 A1 Nov. 17, 2016

(30) Foreign Application Priority Data
Jan. 13, 2014 (EP) .................................... 14150965

(51) Int. Cl.
| | | |
|---|---|---|
| *A61K 39/35* | (2006.01) | |
| *A61K 31/315* | (2006.01) | |
| *A61K 31/295* | (2006.01) | |
| *A61K 47/55* | (2017.01) | |
| *A61K 31/353* | (2006.01) | |
| *C07K 14/47* | (2006.01) | |
| *A61K 39/00* | (2006.01) | |
| *G01N 33/68* | (2006.01) | |
| *G01N 33/92* | (2006.01) | |

(52) U.S. Cl.
CPC ....... *G01N 33/6893* (2013.01); *A61K 31/295* (2013.01); *A61K 31/315* (2013.01); *A61K 31/353* (2013.01); *A61K 39/35* (2013.01); *A61K 47/551* (2017.08); *C07K 14/47* (2013.01); *G01N 33/6863* (2013.01); *G01N 33/92* (2013.01); *A61K 39/00* (2013.01); *G01N 2800/24* (2013.01)

(58) Field of Classification Search
None
See application file for complete search history.

(56) References Cited

U.S. PATENT DOCUMENTS

2011/0268818 A1* 11/2011 Barasch ............... A61K 31/366
424/646

FOREIGN PATENT DOCUMENTS

| WO | WO 94/16068 A2 | 7/1994 |
|---|---|---|
| WO | WO 2006/091035 A1 | 8/2006 |
| WO | WO 2011/053832 A1 | 5/2011 |

OTHER PUBLICATIONS

Ngo et al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994.491-495.*
Skolnick et al. 'From genes to protein structure and function: novel applications of computational approaches in the genomic era.' Trends in Biotech. 18:34-39, 2000.*
Attwood et al. 'The Babel of Bioinformatics.' Science. 290(5491): 471-473.*
Schein et al. 'Bioinformatics approaches to classifying allergens and predicting cross-reactivity.' Immunol. Allergy Clin. North Am. 27(1):1-27, 2007.*
Friedl-Hajek et al. 'Identification of a highly promiscuous and an HLA allele-specific T-cell epitope in the birch major allergen Bet v 1 :HLA restriction, epitope mapping and TCR sequence comparisons.' Clin. Exp. Allergy 29:478-487, 1999.*
Kurucz etal. 'Current Animal Models of Bronchial Asthma.' Curr. Pharm. Des. 12:3175-3194, 2006.*
Mukherjee et al. 'Allergic Asthma: Influence of Genetic and Environmental Factors.' J. Biol. Chem. 286(38):32883-32889, 2011.*
www.allergen.org/Cynodon dactylon Jan. 1, 2010.*
www.allergen.org/Cyn d 2 Jan. 1, 2010.*
Golonka et al. 'The Iron Tug-of-War between Bacterial Siderophores and Innate Immunity.' J Innate Immun. 11(3):249-262, 2019. doi: 10.1159/000494627. Epub Jan. 3, 2019.*
Leopoldini et al. 'Iron Chelation by the Powerful Antioxidant Flavonoid Quercetin.' J. Agric. Food Chem. 54, 6343-6351, 2006.*
Kristiansen et al. 'Allergen immunotherapy for the prevention of allergy: A systematic review and meta-analysis.' Pediatr Allergy Immunol. Feb. 2017;28(1):18-29. doi: 10.1111/pai.12661. Epub Dec. 12, 2016.*

(Continued)

*Primary Examiner* — Nora M Rooney
(74) *Attorney, Agent, or Firm* — Birch, Stewart, Kolasch & Birch, LLP

(57) ABSTRACT

Disclosed is a method for diagnosing allergy in a human or animal patient, wherein the level of species-specific lipocalin, especially lipocalin 2 in a human patient, is measured in a sample of said patient and wherein a lowered level of said lipocalin compared to the level of said lipocalin in the corresponding sample of a human or animal that has no allergy, is indicative of an allergy, as well as a kit for performing this method, and a kit for quality control of allergen molecules or extracts used for immunotherapy of allergy by determining its siderophore-iron ligand load and thus immunomodulatory potency. Further, lipocalin proteins for use in treatment or prevention of allergies are provided, preferably complexed with siderophore-iron ligands.

12 Claims, 6 Drawing Sheets

(56) References Cited

OTHER PUBLICATIONS

Figure 1:
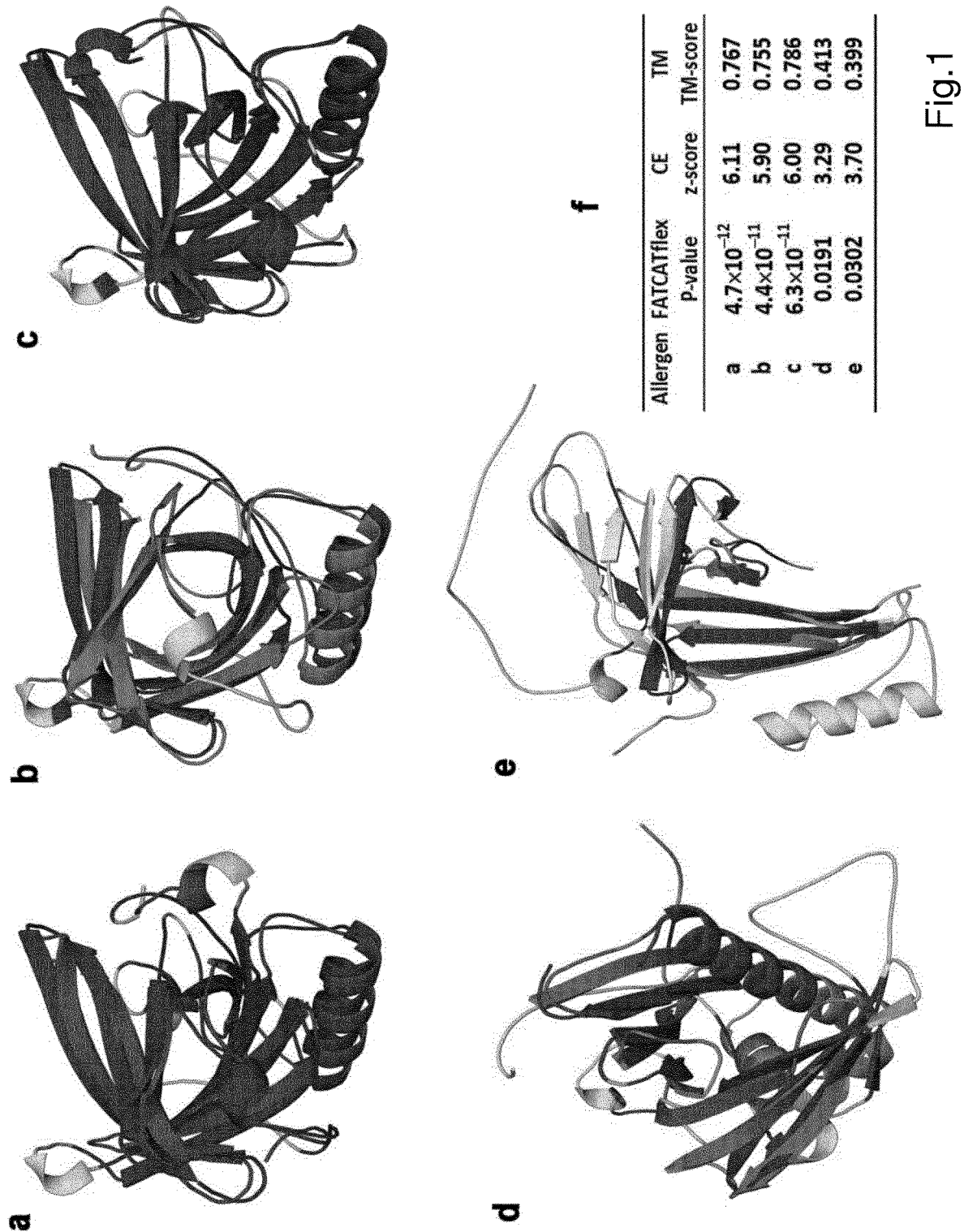

Martignago et al. 'Preventive actions of allergen immunotherapy: the facts and the effects in search of evidence.' Clin Mol. Allergy 2017; 15: 13. Published online Jun. 15, 2017. doi: 10.1186/s12948-017-0070-7.*
Roth-Walter et al. 'Bet v 1 from Birch Pollen Is a Lipocalin-like Protein Acting as Allergen Only When Devoid of Iron by Promoting Th2 Lymphocytes.' J. Biol. Chem. 289(25): 17416-17421, 2014.*
Flower et al. 'The lipocalin protein family: structural and sequence overview.' Biochimica et Biophysica Acta 1482:9-24, 2000.*
http://allergen.org/viewallergen.php?aid=464 Jun. 13, 2020.*
Schou et al. 'Defining allergens of mammalian origin.' Clin. Exp. Allerg. 23:7-14, 1993.*
Hilger et al. 'Animal lipocalin allergens.' Curr Allerg. Asthma Rep. 12:438-447, 2012.*
Maazi et al. 'Iron administration reduces airway hyperreactivity and eosinophiliain a mouse model of allergic asthma.' Clinical and Experimental Immunology, 166: 80-86, 2011.*
Austin et al., "A community randomized controlled clinical trial of mixed carotenoids and micronutrient supplementation of patients with acquired immunodeficiency syndrome", European Journal of Clinical Nutrition (2006) 60, pp. 1266-1276.
Casado et al., "Modeling iron-catecholates binding to NGAL protein", Journal of Molecular Graphics and Modelling 45 (2013), pp. 111-121.
Cox et al., "Allergen immunotherapy: A practice parameter third update", J Allergy Clin Immunol, Jan. 2011, vol. 127, No. 1, pp. S1-S55.
Dittrich et al., "Lipocalin2 protects against airway inflammation and hyperresponsiveness in a murine model of allergic airway disease", Clinical Experimental Allergy, 40, pp. 1689-1700.
Edlmayr et al., "Allergen-Specific Immunotherapy: Towards Combination Vaccines for Allergic and Infectious Diseases", Current Topics in Microbiology and Immunology (2011 ) 352: pp. 121-140.
European Search Report for EP 14150965.3 dated Apr. 11, 2014.
Ferreira et al., "Customized Antigens for Desensitizing Allergic Patients", Advances in Immunology, vol. 84, pp. 79-129.
Flower et al., "Structure and sequence relationships in the lipocalins and related proteins", Protein Science (1993), 2, pp. 753-761.
Flower et al., "The lipocalin protein family: structural and sequence overview", Biochimica et Biophysica Acta 1482 (2000), pp. 9-24.
Focke-Tejkl et al., "Safety of engineered allergen-specific immunotherapy vaccines", Curr Opin Allergy Clin Immunol. Oct. 2012; 12(5), pp. 1-17.
Hall et al., "Essential Role for Retinoic Acid in the Promotion of CD4* T Cell Effector Responses via Retinoic Acid Receptor Alpha", Immunity 34, Mar. 25, 2011, pp. 435-447.
Hider et al., "Chemistry and biology of siderophores", Nat. Prod. Rep., 2010, 27, pp. 637-657.
International Search Report for PCT/EP2015/050126 dated Feb. 9, 2015.
Jackson et al., "Prevalence of house dust mites and dermatophagoides group 1 antigens collected from bedding, skin and hair coat of dogs in south-west England", Veterinary Dermatology 2005, 16, pp. 32-38.
Kiefer et al., "The Swiss-Model Repository and associated resources", Nucleic Acids Research, 2009, vol. 37, Database issue, pp. D387-D392.
Kinnunen et al., "Potential of an altered peptide ligand of lipocalin allergen Bos d 2 for peptide immunotherapy", Basic and clinical immunology, Apr. 2007, pp. 965-972.
Klimek et al., "Specific subcutaneous Immunotherapy with recombinant grass pollen allergens: first randomized dose-ranging safety study", Article first published online: May 23, 2012.
Liu et al., "Multiple Apoptotic Defects in Hematopoietic Cells from Mice Lacking Lipocalin 24p3", JBC The Journal of Biological Chemistry, vol. 286, No. 23, pp. 20606-20614, Jun. 10, 2011.
Lögdberg et al., "Immunocalins: a lipocalin subfamily that modulates immune and inflammatory responses", Biochimica et Biophysica Acta 1482 (2000), pp. 284-297.
Lu et al., "Characterization of Protective Human $CD4^+CD25^+$ $FOXP3^+$ Regulatory T Cells Generated with IL-2, TFG-13 and Retinoic Acid", Dec. 2010, vol. 5, Issue 12, pp. 1-12.
Mayer et al., "Therapeutic Potential of Oral Tolerance", vol. 4, Jun. 2004, pp. 407-419.
Möller et al., "Cytokines and Acute Phase Reactants During Flare-Up of Contact Allergy to Gold", American Journal of Contact Dermatitis, vol. 9, No. 1, Mar. 1998, pp. 15-22.
Mori et al., "Endocytic delivery of lipocalin-siderophore-iron complex rescues the kidney from ischemia-reperfusion injury", vol. 115, No. 3, Mar. 2005, pp. 610-621.
Pino-Lagos et al., "A retinoic acid-dependent checkpoint in the development of $CD4^+$ T cell-mediated immunity", vol. 208, No. 9, Published Aug. 22, 2011, pp. 1767-1775.
Prlić et al., "Pre-calculated protein structure alignments at the RCSB PDB website", vol. 26, No. 23, 2010, pp. 2983-2985.
Roth-Walter et al., "Pasteurization of milk proteins promotes allergic sensitization by enhancing uptake through Peyer's patches", Allergy 2008: 63: pp. 882-890.
Roth-Walter et al., "Targeting antigens to murine and human M-cells with Aleuria aurantia lectin-functionalized microparticles", Immunology Letters 100 (2005), pp. 182-188.
Schöll et al., "Dimerization of the Major Birch Pollen Allergen Bet v 1 Is Important for its In Vivo IgE-Cross-Linking Potential in Mice", Copyright 2005 by The American Association of Immunologists, Inc., pp. 6645-6650.
Shindyalov et al., "Protein structure alignment by incremental combinatorial extension (CE) of the optimal path", Protein Engineering, vol. 11, No. 9, pp. 739-747, 1998.
Stewart et al., "The biochemistry of common aeroallergens", Clinical and Experimental Allergy, 1996, vol. 26, pp. 1020-1044.
Virtanen et al., "Mammalian lipocalin allergens—insights into their enigmatic allergenicity", Clinical Experimental Allergy, 42, 2011, pp. 494-504.
Virtanen, "Lipocalin allergens", Allergy 2001: 56: Suppl. 67: pp. 48-51.
Wallner et al., "Recombinant Allergens for Pollen Immunotherapy", Immunotherapy, 2013; 5(12): 1323-1338.
Written Opinion of the International Searching Authority for PCT/EP2015/050126 dated Feb. 9, 2015.
Ye et al., "Fatcat: a web server for flexible structure comparison and structure similarity searching", W582-W585, Nucleic Acids Research, 2004, vol. 32, Web Server issue.
Zhang et al., "TM-align: a protein structure alignment algorithm based on the TM-score", Published online Apr. 22, 2005, Nucleic Acids Research, vol. 33, No. 7, pp. 2302-2309.
Zsila et al., "Retinoic acid binding properties of the lipocalin member β-lactoglobulin studied by circular dichroism, electronic absorption spectroscopy and molecular modeling methods", Biochemical Pharmacology 64 (2002), pp. 1651-1660.

* cited by examiner

METHOD AND MEANS FOR DIAGNOSING AND TREATING ALLERGY

The present invention relates to the diagnosis and therapy of allergy.

20% of the industrialized population suffers from allergy, which includes symptoms like allergic rhinoconjunctivitis, dermatitis, bronchial asthma, oral allergy syndrome, angioedema, gastrointestinal symptoms and anaphylactic shocks. However, the etiology of allergic sensitization remains poorly understood.

Allergy diagnosis is based on three main pillars, patient's history, in vitro and in vivo Tests. In vitro tests include determination of total-IgE and allergen-specific IgE levels, whereas in vivo tests include skin prick, intracutaneous tests and oral provocation tests. Both in vivo as well as in vitro methods are necessary to accurate diagnose a patient with allergy. Hence, the development of in vitro methods that reduce the numbers of in vivo methods, would greatly increase patients' compliance and reduce side effects.

Only causative treatment against allergies is allergen immunotherapy by the sublingual or subcutaneous route. During allergen immunotherapy increasing doses of allergen are applied, resulting in the generation of antibody-classes other than IgE. Successful immunotherapy is often accompanied with decreased levels of allergen-specific IgE and increased IgG4-levels.

The efficacy of allergen immunotherapy however varies dependent on the allergens used, in particular because the exact mechanisms of desensitization remain poorly understood or are under current investigations. An important role in desensitization has been attributed to a counterregulation of the Th2-cytokine milieu, which leads to a decrease of allergen-specific IgE-levels. Furthermore, a reduced allergen-specific T cell response is observed, which optimally leads to the generation of regulatory T-cells.

Hence, methods, which would result in an anti-allergic immune modulation or immune tolerance, clearly need to be developed (Roth-Walter et al., Immunol. Lett. 2005; 100: 182-188; Roth-Walter et al., Allergy 2008; 63: 882-890).

Why people or animals become allergic still remains elusive. Even though the past decades have produced myriad information regarding the effector phase of allergic diseases, very few information is available concerning the sensitization phase.

Most studies on allergic disease, be it on respiratory, skin or ingested antigens, is done in models where sensitization is achieved via intraperitoneal application of suitable proteins, a route hardly representative of sensitization process in humans or animals.

However, despite the existence of several thousands of protein families, most allergens belong to a rather limited number of protein families. So the vast majority of aeroallergens deriving from animals belong to the lipocalin-family (Virtanen, Allergy 2001; 56 Suppl 67: 48-51) and plant allergens usually originate from the prolamin or cupin superfamilies and the Bet v 1 family. All of these families are able to bind to lipids and fatty acids. They are either multimeric proteins or tend to form aggregates (Schoell et al, Journal of Immunology 2005; 175: 6645-6650). The majority of allergens can also be classified by their biological function having either 1) proteolytic, 2) enzyme inhibitory activity or 3) transport function (Stewart et al., Clinical and Experimental Allergy 1996; 26: 1020-1044).

In contrast to humans, the specific proteins to which animals patients are allergic are less well defined, since tests are usually performed using extracts containing a variety of proteins. However, dogs and other mammalians seem to have similar IgE-reactivity to same allergen epitopes as humans and can also be allergic to other animals like mites, cats, ticks and even to humans. Also here major allergens have been found to be lipocalins (Jackson et al., Veterinary Dermatology 2005; 16: 32-38).

It is an object of the present invention to provide diagnostic and therapeutic tools, especially for improving current diagnostic and therapeutic techniques for human and animals suspected to have allergy or suffering from allergy, thereafter termed patients. A more specific object is to provide biomarker monitoring for the course and success of allergen immunotherapy.

Therefore, the present invention provides a method for diagnosing allergy in a human or animal patient, wherein the level of species-specific lipocalin (in humans lipocalin 2) is measured in a sample of said patient and wherein a lowered level of said lipocalin compared to the level of said lipocalin in the corresponding sample of a human or animal that has no allergy, is indicative of an allergy.

Moreover, the invention also provides the application of exogenous or endogenous (self) lipocalins such as LCN2 for humans and animals for immunotherapy. More specifically, the level of lipocalins loaded with ligands in their molecular pocket such as siderophores with or without iron, or retinoic acid, determined by the method of the present invention has predictive value for the success of prophylactic immunotherapy (vaccine) or therapeutic immunotherapy of allergy, for the monitoring of allergen immunotherapy or the quality standardization of allergen extracts and allergen molecules applied for immunotherapy in patients.

The term "species-specific lipocalin" according to the present invention is understood as being an autologous lipocalin protein being in principle present in and encoded and expressed by the genome of the species concerned, for example lipocalin 2 in humans or other species-specific lipocalins as disclosed in table 1.

The present invention is based on the teaching that lipocalin 2 (neutrophil gelatinase-associated lipocalin (NGAL=LCN2=24p3)) level is indicative of the presence of allergy and/or to determine sensitization state in allergic human and pet individuals. The present method is therefore suitable to diagnose allergy by measuring lipocalin 2 in a sample of an individual whose status with respect to allergy has to be determined. According to the present invention, a lowered lipocalin 2 level (compared to a "healthy" (i.e. proven non-allergic) individual) is indicative for the presence of allergy. With the present invention, a diagnostic tool is provided that allows i) a more accurate allergy diagnosis, ii) with a low sample volume only, iii) reducing the numbers of diagnostic skin prick tests, thereby increasing patients' compliance. For example, in the method according to the present invention less than 10 μl serum is necessary for analysing lipocalin 2 levels, whereas for other tests (such as the ISAC ImmunoCAP method), at least 50 μl to 100 μl blood are necessary.

Lipocalin has been suggested as a therapeutic agent against cancer metastasis in WO 2006/091035 A1. WO 2011/053832 A1 discloses the use of urinary NGAL to diagnose sepsis in very low birth weight infants. Möller et al. (AM. J. Cont. Derm. 9 (1998), 15-22) describes cytokines and acute phase reactants during flare-up of contact allergy to gold. Dittrich et al. (Clin. Exp. Allergy 40 (2010), 1689-1700) report that Lipocalin 2 protects against airway inflammation and hyperresponsiveness in a murine model of allergic airway disease. Ferreira et al. (Ad. Immunol. 84 (2004), 79-129) teach that recombinant allergens are superior to allergen extracts for desensitizing allergic patients. Kinnunen et al. (J. All. Clin. Immunol. 119 (2007), 965-972) show that altered peptide ligands of lipocalin allergen Bos d2 can be beneficial for peptide immunotherapy. WO 94/16068 A2 teaches that recombinant allergens from dog dander have advantageous properties. These documents show the clear prevalence of recombinant allergens as promising therapeutic lead substances in the field of allergy (and as a replacement for allergens derived from natural sources). Further—most recent—examples for this trend is Wallner et al. (Immunother. 5 (2013), 1323-1338), Edlmayr et al. (Curr. Top. Microbiol. Immunol. 352 (2011), 121-140) and Focke-Tejkl et al. (Curr. Opin. All. Clin. Immunol. 12 (2012), 555-563).

Mori et al. (J. Clin. Invest. 115 (2005), 610-621) report that endocytic delivery of lipocalin-siderophore-iron complex rescues the kidney from ischemia-reperfusion injury.

The present invention is based on the lipocalin function in the immune system. According to the present invention, a subset of the lipocalins exerts significant immunomodulatory effects in vitro and in vivo. Interestingly, in humans most lipocalins are found in the q32-34 region of human chromosome 9 and seem to exert anti-inflammatory functions (Lögdberg et al., Biochimica et biophysica acta 2000; 1482: 284-297). Indeed, murine lipocalin-2 (=24p3=NGAL) has been demonstrated to be an important regulator in hematopoietic cell homeostasis. There are however conflicting data concerning its pro- or anti-apoptotic activities on lymphocytes, monocytes and erythrocytes (Liu et al., The Journal of Biological Chemistry 2011; 286: 20606-20614). Lipocalin 2 (=NGAL) is an iron-trafficking protein involved in multiple processes such as apoptosis, innate immunity and renal development. The iron-free form termed apo-lipocalin 2 seems to be anti-apoptotic, but also contrary results have been reported with lipocalin 2 being pro-apoptotic in its iron-free form and anti-apoptotic as holo-lipocalin 2. Despite the controversial data, it is clear that lipocalin 2 still has a profound impact on immune cells, as lipocalin 2-knockout mice have apoptotic defects that seem to be restricted to relatively mature blood cell compartments. Moreover, it was demonstrated that under immune-suppressive conditions bone marrow-derived dendritic cells secrete high amounts of lipocalin-2. Lipocalin-2 is highly expressed in bone marrow and in barrier tissues that are prone to exposure to microorganism like salivary gland, colon and lung. In this respect, it is striking to note that on the one side practically all respiratory allergens deriving from animals are lipocalins and that on the other side the lung is a site, where lipocalin-2 itself is highly expressed.

A further molecule that interacts with lipocalins is retinoic acid (Zsila et al, Biochem. Pharmacology 64 (2002) 1651-1660). Thereby lipocalins can acquire immunomodulatory function on CD4+ T-cells (Austin et al, European Journal of Clinical Nutrition (2006) 60, 1266-1276; Hall et al, (2011) Immunity 34, 435-447; Lu et al, PLOS one (2010) 5; 12: e15150; Pino-Lagos et al, J. Exp. Med. (2011) 208; 9: 1767-1775).

The present invention also provides a method for the quantitative and qualitative determination of the iron-load of endogenous lipocalin or exogenous lipocalin allergens that is suitable for quality determination of a lipocalin, an allergen extract or allergen molecule determined for prophylactic or therapeutic immunotherapy of allergy.

"Allergy" according to the present invention is preferably understood as IgE mediated type I allergy and preferably excludes immunoglobulin independent T cell reactive type IV allergies (e.g. contact allergies). Contact allergies (Th1 and cytotoxic T cells) are mechanistically completely distinct and remote from IgE mediated (Th2) allergies (which are in the center of the present invention).

According to the present invention the level of lipocalin 2 or lipocalin 2 mRNA is quantitatively determined by immunoassays such as Enzyme-linked Immunosorbent Assay (ELISA) or polymerase chain reaction (PCR) in any biological sample that can be taken from an individual suspected of having allergy.

Preferred samples are those that can easily be provided from the patients and that allow a specific testing of lipocalin 2 protein or mRNA. Preferably, the sample is a body fluid, selected from blood, serum, plasma, urine, tear fluid, lymph, mucus, or saliva, or easily accessible samples, such as hair and dander wherein lipocalin 2 is also present. In these body samples, the lowering of lipocalin 2 in allergy patients or changes of lipocalin 2 during an allergy immunotherapy is easily detectable without major efforts or problems for the patient. Specifically preferred, the body fluid is blood, serum or plasma and the patient is a human patient. The patient may also be a veterinarian patient, preferably dog, cat, or horse. Blood or blood derived samples of human or veterinarian patients are easily available and providable also for routine testing.

In a typical immunoassay, in parallel to the patient sample testing "standard" Lipocalin-2 is applied in a known concentration, (e.g. 10-50 ng per test), or applied serially diluted (e.g. 10, 20, 50, 100, 200, 500 ng or 1 µg per test) in duplicates or triplicates, to generate a standard calibration curve. Then the measurement results of the patient sample are compared to the standard Lipocalin-2 in order to determine the relative amounts of Lipocalin 2 in the biological sample. The sample itself may be applied directly onto the solid phase or applied to a precoated "catching antibody" to Lipocalin-2. Bound Lipocalin-2 is then detected by a (second) anti-Lipocalin-2 antibody which is directly labeled by an enzyme (to be developed by addition of a substrate) or fluorophor. The resulting emission or absorbance is read in an electronic device suitable for the method, e.g. an ELISA reader at absorbance/emission optimal for the detection reagent. The signal intensity is directly proportional to the measured Lipocalin levels. A reduced Lipocalin-2 level would be indicative for allergy.

Lowering of lipocalin 2 levels in allergy patients compared to non-allergy individuals is significant and therefore suitable for routine testing of allergy patients, even for large scale testing or routine diagnostics.

For example, the level of lipocalin 2 is lowered by at least 5% (with respect to the ng lipocalin 2/ml body fluid), preferably by at least 10%, especially at least 15%, compared to the level of lipocalin 2 in the corresponding sample source of a human or animal that has no allergy (defining the 100% level).

According to a preferred embodiment, the level of lipocalin 2 according to present invention is determined by immunological techniques, such as ELISA, ELISPOT, immunoblot, other solid phase assays, using e.g. radioactivity, fluorescence, chemiluminescence, etc.; alternatively, also the level of mRNA in the sample can be measured e.g. by (real time) PCR; specifically as only minimal amounts of material are needed according to the present invention.

According to another aspect, the present invention also provides a kit for performing a method according to the present invention, comprising
 means for detecting the level of lipocalin 2, especially a molecule binding to lipocalin 2, and means for comparing the level of lipocalin 2 to be detected with the level of lipocalin 2 in a human or animal that has no allergy.

The kit may be packaged in a sterile sale unit for diagnostic testing. The sale unit may be a single test sale unit or a multiple test sale unit (e.g. a sale unit with 5, 10 or 20 single tests in one sale unit). Preferably, all necessary components and information (product leaflets, instructions for use, etc.) are also provided in the sale unit. The test itself has not to be done in sterile condition and hence is ready to use.

In a preferred embodiment of the kit according to the present invention, the means for detecting the level of lipocalin 2 is a species-specific anti-lipocalin antibody or a lipocalin binding antibody fragment, especially an anti-human lipocalin 2 antibody or a human lipocalin 2-binding antibody fragment. If various animal samples are determined, the corresponding antibodies against the homologous (species-specific) lipocalin 2 polypeptides are preferably used, e.g. anti-canine lipocalin 2, anti-equine lipocalin 2 and anti-feline lipocalin 2 antibodies.

Examples of antibody fragments of the invention include (A) a "half antibody" molecule, i.e. a single heavy:light chain pair, and (B) an antibody fragment, such as the univalent fragments Fab and the divalent fragment $F(ab')_2$, and a single or double chain variable fragment, Fv. Antibody fragments according to the invention are preferably Fab fragments or antigen-binding regions such as sFv. Many kind of antibodies and antibody fragments are known in the art. Antibodies according to the invention include human antibodies, humanized antibodies, chimeric antibodies, mammalian antibodies like murine antibodies, rat antibodies, camel antibodies; shark antibodies, and other antibodies of various animal sources known in the art.

Humanized antibodies are chimeric antibodies comprising non-human and human regions, and have reduced immunoreactivity when used therapeutically in humans. Typically, the variable domains or are of non-human origin and the constant domains are of human origin. Humanized antibodies can also be produced by inserting non-human complementarity-determining-regions (CDRs) into the framework of a human antibody. An antigen binding site in an antibody is made up of CDRs in the light chain and CDRs in the heavy chain. Humanized antibodies can be produced using recombinant DNA technology well-known in the art. Briefly, oligonucleotides encoding CDRs with desired antigen-recognition properties are used to replace the CDR regions in a human antibody gene. In certain instances, a mouse monoclonal antibody will have the desired antigen-recognition characteristics. These CDR-encoding regions are sequenced and oligonucleotides encoding these regions are inserted into the human antibody gene. Such techniques for humanization of antibodies and cloning antibody (immunoglobulin) genes are well known in the art.

A fragment according to the present invention can be an Fv fragment. An Fv fragment of an antibody is made up of the variable region of the heavy chain (Vh) of an antibody and the variable region of the light chain of an antibody (Vl). Proteolytic cleavage of an antibody can produce double chain Fv fragments in which the Vh and Vl regions remain non-covalently associated and retain antigen binding capacity.

Double chain Fv fragments also can be produced by recombinant expression methods well known in the art. Briefly, the amino acid sequence of the variable regions of the heavy and light chains of antibodies known in the art can be obtained by direct amino acid sequencing using methods well known to those in the art. From this amino acid sequence, synthetic genes can be designed which code for these variable regions and they can both be inserted into an expression vector. Alternatively, nucleotide sequences known in the art that encode antibodies can be employed. Two polypeptides can be expressed simultaneously from a mammalian or bacterial host, resulting in formation of an active Fv fragment.

An antibody fragment of the present invention also can be a single-chain molecule or so-called "single chain antigen binding polypeptide," a phrase used in this description to denote a linear polypeptide that binds antigen with specificity and that comprises variable or hypervariable regions from the heavy and light chain chains of an antibody. Single chain antigen binding polypeptides that retain an antigen-binding capacity that is characteristic of the present invention can be produced by conventional methodology. The Vh and Vl regions of the Fv fragment can be covalently joined and stabilized by the insertion of a disulfide bond. Alternatively, the Vh and Vl regions can be joined by the insertion of a peptide linker. A gene encoding the Vh, Vl and peptide linker sequences can be constructed and expressed using a recombinant expression vector. Amino acid sequences comprising hypervariable regions from the Vh and Vl antibody chains can also be constructed using disulfide bonds or peptide linkers.

Besides monoclonal antibodies or other (recombinantly) produced antibodies, also polyclonal antibodies specific for lipocalin 2 may be applied in the present invention.

The kit according to the present invention may further comprise a marker (e.g. biotin, digoxygenin), which can be preferably detected by colourigenic, fluorescent, luminescent, magnetic or radioactive means, especially a marker that is covalently linked to the means for detecting the level of lipocalin 2 or a marker that is covalently linked to the molecule binding to lipocalin 2.

For example, the lipocalin 2-specific antibody or antibody fragment may further include a radionuclide, enzyme, substrate, cofactor, fluorescent marker, chemiluminescent marker, peptide tag, or a magnetic particle. The marker may be detectable by techniques well known in the art, for example by colorimetry, fluorescence, scintigraphy, PET scan, NMR or X-rays. A preferred marker is biotin. The marker may also be present on a further detection molecule for the lipocalin 2 binding molecule, such as a secondary antibody (or antibody fragment) binding to the (first) species-specific lipocalin 2-specific antibody or antibody fragment.

Alternatively, for the detection of the iron load of endogenous or exogenous lipocalin allergens, the autofluorescence of the molecule, respectively the quenching of this signal by addition of ligands, can be determined in relation to unloaded lipocalin.

Preferably, the kit according to the present invention further comprises one or more standards for lipocalin 2.

Another preferred embodiment of the kit of the present invention is the use of siderophores/ligand preparation with a defined amount of ligand/siderophore, where the ligand itself can be detected directly or indirectly e.g. by fluorescent, colorogenic chemiluminescent or radiological means.

According to this aspect, the present invention provides a method for determining the quantity of unloaded lipocalin 2. This quantity can be determined directly or indirectly. In the direct method the addition e.g. of an unlabeled siderophore results in quenching of the autofluorescence of lipocalin proteins. If in the indirect method a chromogenic, fluorogenic, chemilumenscenic siderophores is added it may compete with the bound siderophores or extract ligands from siderophores re-establishing the intrinsic autofluorescence of lipocalin proteins. The delta in signal intensity is then indirectly correlated to the amount of ligand loaded in the siderophore.

In these ligand-binding assays according to the present invention, siderophores loaded with iron or other ligands such as retinoic acid can be specifically used for testing lipocalin allergens. Quenching of the autofluorescence of lipocalin allergens can be determined spectrophotometrically. In the direct assays, the signal upon incubation with the test siderophore or retinoic acid is inversely related to the natural loading of the lipocalin allergen; in the competitive assay, the signal upon incubation with the test siderophore or retinoic acid is directly related to the already bound ligand in the lipocalin allergen. For example, measurement of autofluorescence for the detection of the ligand-load of lipocalin allergens can be performed in relation to unloaded lipocalin. Hence the method of this invention allows classification of lipocalin allergens as holo- or apo-forms.

Accordingly, the present invention also relates to a method for determining the quantity of unloaded lipocalin 2 in a lipocalin 2 containing preparation wherein
(a) either a predetermined amount of test siderophore is added to the preparation or
(b) the preparation is competitively tested with iron-ligands not able to bind to the lipocalin cavity, preferably desferral, that extracts ligands from the lipocalin-pocket resulting in the reestablishment of the intrinsic fluorescence of the proteins; or
(c) fluorescent, chromogenic, radiolabelled siderophore-iron-complexes are used directly or competitively for binding to the lipocalin cavity
and wherein the quantity of unloaded lipocalin 2 is determined by (a) quenching of the autofluorescence of lipocalin proteins
(b) autofluorescence of lipocalin proteins, or
(c) measurement of bound siderophore.

Therefore, the present invention also relates to a method for determining the quantity of unloaded lipocalin allergen or lipocalin 2 in a preparation wherein
(a) either a predetermined amount of siderophore, like 2,3, dihydroxybenzoic acid, is added to the preparation or
(b) the preparation is competitively tested with iron-ligands not able to bind to the lipocalin cavity, like desferral, that extracts ligands from the lipocalin-pocket resulting in the reestablishment of the intrinsic fluorescence of the proteins at excitation/emission of 280/340 nm.

According to another aspect, the present invention is drawn to lipocalin proteins for use in treatment or prevention of allergies, wherein the lipocalin is administered in the holo-form. The "holo-form" of lipocalin is defined as the combination of the lipocalin protein and a siderophore loaded with a metal ion, especially an $Fe^{3+}$ ion. According to the teachings of the present invention only the holo-form turned out to be successfully applicable in efficient treatment or prevention of allergies. Only the holo-form showed efficient immunosuppressive properties, in contrast to the apo-form (without siderophore/$Fe^{3+}$). Accordingly, only recombinant lipocalin allergens that have been supplied with a sufficient amount of siderophores and Fe ions are suitable according to the present invention. When naturally (i.e. non-recombinant; from natural sources) harvested single allergens are used in the method according to the present invention, care must be taken that siderophore and metal ions are either conserved in the preparation or supplemented to the final product to be administered to a patient, because usual purification methods leading to single allergens also eliminate siderophore and metal ion from the lipocalin allergen so that only the apo-allergen is obtained.

The present invention therefore provides a therapeutic method of treating, reducing, or ameliorating clinical manifestations of allergic disease by administering to the allergy patient lipocalin 2 or other lipocalin allergens in an amount effective to treat, reduce or ameliorate allergic disease. According to the present invention it is mandatory that lipocalin 2 or other lipocalin allergen is administered in the holo-form (as holo-lipocalin 2 or holo-lipocalin allergen). Therefore, the lipocalin 2 or other lipocalin allergen is present together with a siderophore combined with a metal ion so that it can be co-administered with the lipocalin allergen. Up to now, when allergen immunotherapy was performed with single allergen molecules, this was done with iron-free lipocalins, as the siderophores are lost during production and purification. However, the apo-form has the undesirable intrinsic property to cause a Th2-shift by promoting CD4+ immune cells. It is also necessary that the holo-lipocalin 2 or other holo-lipocalin allergens are administered in purified form, i.e. as single allergen molecules (or mixtures of recombinant or purified single allergen molecules) and, however, less preferred, in the form of allergen extracts. The present invention therefore relies on immunotherapy against allergy, where lipocalin-allergens are administered in combination with iron-siderophores (=holo-lipocalin), thereby blocking the Th2-skewing properties of lipocalin allergens and allowing the more efficient generation of immune tolerance.

Most of the important mammal-derived respiratory allergens, as well as the major milk allergen and a few insect allergens, belong to the lipocalin protein family as depicted in Table 1. Lipocalins were initially defined as powerful bacteriostatic agent active against various Gram-negative microorganisms through impeding iron sequestration. They are involved in a variety of biological processes like immune regulation, pheromone transport, prostaglandin synthesis and lipid transport. Lipocalin 2 has also been identified as a stress protein that is released under various inflammatory conditions and cancer. Lipocalins vary greatly on the sequence level with unusually low levels of overall sequence conservation and pairwise comparison often falling below 20%. Nevertheless, the lipocalin crystal structures are very well conserved (Flower et al., Protein Science 1993; 2: 753-761). The lipocalin fold consists of an antiparallel β barrel structure made of eight β sheets arranged in an antiparallel orientation resulting in a cup-shaped cavity (the "calyx") that binds, transports, and delivers small ligands (Flower et al., Biochimica et Biophysica Acta 2000; 1482: 9-24). Lipocalins are usually secreted and can be found in the dander, urine, fur and saliva of animals and humans.

Figure 3:
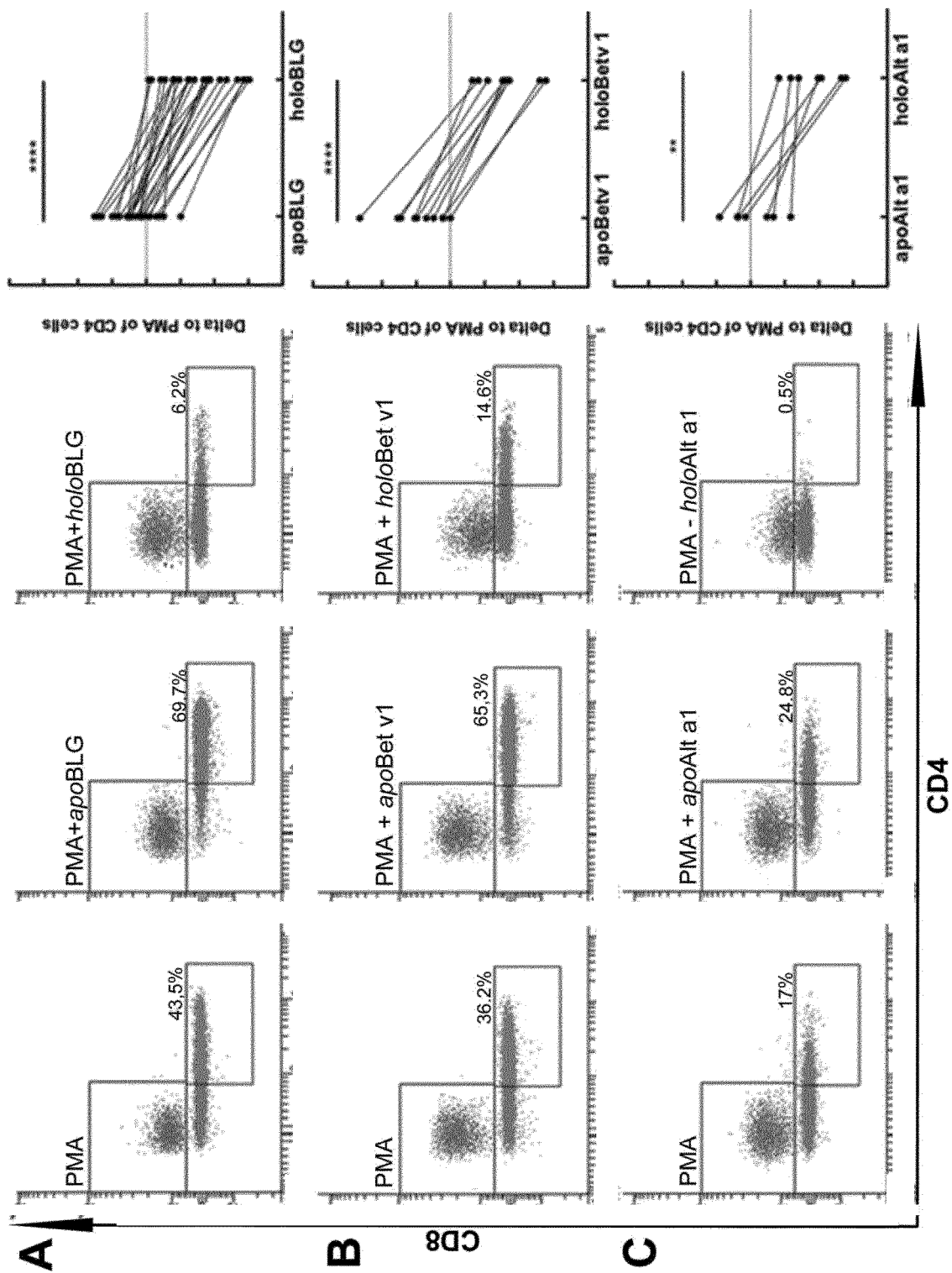

Lipocalin allergens induce T helper type 2 (Th2) deviation, when devoid of iron, but the reasons for this are enigmatic. Mammalian lipocalins are thought to be on the borderline of self and non-self and hence to be able to amount a Th2-response under so far elusive circumstances (Virtanen et al., Clinical and Experimental Allergy 42 (2011), 494-504). It was recently discovered lipocalin allergens can mimic human lipocalin 2 and increase survival in the apo-form, thereby being anti-apoptotic to CD4+ cells, whereas the holo-form severely impaired the expression of CD4+ cells on peripheral blood mononuclear cells (see also: FIG. 3). Moreover, significant structural homologies with other major inhalative allergens like Bet v 1 and Alt a 1 with the lipocalin-family were identified, providing the lipocalin-structure as a general characteristics for most inhalative allergens (see also: FIG. 1). "Lipocalin proteins" according to the present invention are (human) lipocalin 2 and naturally occurring lipocalin-like proteins having sequential topology of eight antiparallel beta-strands and forming a cavity capable of binding siderophore-iron complex. With the present invention, the similar lipocalin structure of major allergens has been proven, specifically the allergens explicitly referred to hereinafter.

TABLE 1

Lipocalins. The sequential identity of lipocalins varies but the three-dimensional structure is conserved. They are present in body fluids and secretions and other samples of human and animal individuals.

Lipocalins as allergens

| | |
|---|---|
| Bug | Tria p 1 |
| cat | Fel d 4 |
| Cockroach | Bla g 4 |
| cow | Bos d 2, Beta-lactoglobulin Bos d 5 |
| dog | Can f 1 and Can f 2 |
| guinea pig | Cav p 1, Cav p 2, Cav p 3 |
| horse | Equ c 1, Equ c 2.0101 and Equ c 2.0102 |
| mite | Der p 2, Aca s 13, Bt6, Lep d 13 |
| mouse | Mus m 1 |
| rat | Rat n 1 |
| rabbit | Ory c 1 |
| tick | Arg r 1 |

With the present invention, lipocalin proteins are used to treat allergy; such "allergy treatment" also includes a reduction and amelioration of allergy symptoms.

According to the present invention, the lipocalin proteins are administered mandatorily in combination with metal-ions, preferably Fe, Zn, Cu, Se or Mn ions, especially iron $Fe^{3+}$.

In a preferred embodiment, the lipocalin proteins are administered in combination with siderophores, especially siderophores that are complexed with iron.

Lipocalin 2 or other lipocalin proteins as defined herein, especially Der p 2, Bet v 1 and Alt a 1 and all mammalian lipocalin allergens, cannot bind iron directly, but via siderophores. Siderophores are Fe(III)-specific chelating agents in an organisms like catechols and are also produced in the human body (e.g. adrenalin), but also by bacteria to invade the host, which enable them not only to bind to free available Fe(III) but also extract it from iron-binding proteins of the host. Siderophores (Greek: "iron carrier") are small, high-affinity iron chelating compounds and are amongst the strongest soluble $Fe^{3+}$ binding agents known. Siderophores can be secreted by microorganisms such as bacteria, as well as fungi and grasses. Siderophores usually form a stable, hexadentate, octahedral complex preferentially with $Fe^{3+}$ compared to other naturally occurring abundant metal ions, although if there are less than six donor atoms water can also coordinate. The most effective siderophores are those that have three bidentate ligands per molecule, forming a hexadentate complex and causing a smaller entropic change than that caused by chelating a single ferric ion with separate ligands. A comprehensive list of siderophores is presented in Hider et al., Nat. Prod. Rep. 27 (2010), 637-657. $Fe^{3+}$ is a hard Lewis acid, preferring hard Lewis bases such as anionic or neutral oxygen to coordinate with. Microbes usually release the iron from the siderophore by reduction to $Fe^{2+}$ which has little affinity to these ligands.

Siderophores are usually classified by the ligands used to chelate the ferric iron. The major groups of siderophores include the catecholates (phenolates), hydroxamates and carboxylates (e.g. citric acid or derivatives of citric acid). The wide variety of siderophores may be due to evolutionary pressures placed on microbes to produce structurally different siderophores which cannot be transported by other microbes' specific active transport systems, or in the case of pathogens deactivated by the host organism.

Lipocalin 2 exerts its bacteriostatic effect by binding to bacterial siderophores as this lipocalin is released from the liver and spleen in response to an acute bacterial infection. There are several bacterial siderophores however that cannot be trapped in the lipocalin 2-calyx like desferal and pyoverdine and as a consequence allow bacteria to establish infections in the lung. Desferal is used to treat acute iron poisoning, especially in small children. This agent is also frequently used to treat hemochromatosis, a disease of iron accumulation that can be either genetic or acquired. Apart from iron toxicity, deferoxamine can be used to treat aluminium toxicity (an excess of aluminium in the body) in select patients.

Lipocalin proteins are co-administered according to the present invention in combination with siderophores as a complex. "Complex" is understood herein in the usual manner, as non-covalent binding (H-bridges, van der Waals forces and electrostatic interactions) (see e.g. Gomez Casado et al., J. Mol. Graph. Mod. 45 (2013), 111-121).

Preferably, the lipocalin proteins are administered together with a metal-ion, preferably iron complexed with siderophores, in a molar ratio of 0.5 to 3 to 3 to 0.5, preferably in a molar ratio of 1 to 3 to 3 to 1, especially in a molar ratio of 2.0 to 3 to 3 to 2.

According to a preferred embodiment of the present invention, lipocalin proteins are administered with zinc-, copper-, selen-, or mangan-ions.

It is preferred to administer lipocalin proteins with siderophores selected from catechols, catechol-derivatives (compounds containing a benzene ring with two hydroxyl groups in ortho substitution). Preferably, the catechol (1,2-benzenediol) has further side chains, especially on positions 3, 4, 5 and/or 6, especially on positions 2, 4 and 5. Also siderophores like α-hydroxycarboxylate, hydroxyphenyloxazolone, hydroxamate, α-aminocarboxylate, hydroxypyridinone, α-hydroxyimidazole and derivatives thereof can be administered with the lipocalin proteins.

Preferred lipocalin proteins to be used for the treatment according to the present invention are selected from human lipocalin 2, Amb a 1, Aln g 1, Aca s 13, Act c 8, Act d 8, Act d 11, Alt a 1, Asp f 1, Asp f 3, Asp f 6, Art v 1, Api g 1, Api m1, Act d 2, Act d 8, Ara h 8, Arg r 1, Ber e 1, Bet v 1, Bet ch 1, Bet co 1, Bet le 1, Bet n 1, Bet p 1, Blo t5, Bla g 1, Bla g 4, Bos d 2, Bos d 5, Bub b BLG, Can f 1, Canf 2, Can f 6, Cap h BLG, Car b 1, Cas s 1, Cav p 1, Cav p 2, Cav p 3, Cla h 8, Cyn d 1, Cyn d 2, Cyn d 15, Cor a 1, Cor he 1, Che a 1, Cup a 1, Dac g 1, Dac g 2, Dac g 3, Dau c 1, Der p 2, Der f 2, Der f 13, Der p 13, Ecqu c 1, Ecqu c 2, Fag s 1, Fra a 1, Fel d 4, Fel d 7, Gly m 4, Hol l 1, Hom s TL, Hev b 8, Jug r 2, Lep d 13, Lol p 1, Lol p 2, Lol p3, Lyc e 4, Mal d 1, Mer a 1, Mus m 1, Ole e 1, Ory c 1, Ory s 1, Ost c 1, Ovi a BLG, Pas n 1, Pha a 1, Per a 4, Pru ar 1, Pru av 1, Pru p 1, Phl p 1, Phl p 2, Phl p 3, Phl p 11, Pla a 2, Poa p 1, Poa p2, Que a 1, Rant t BLG, Rat n 1, Rub I 1, Sal k 1, Sus s 1, Tri a 1, Tri a 2, Tria p 1, Tyr p 13, Ves v 5, Vig r 1, Zea m 1, Zea m3 and lipocalins of insects, ticks, spiders and fungi.

The treatment of the present invention can be performed in the usual manner of immunotherapies (see e.g.: Cox et al, Task Force Report Journal of Allergy and Clinical Immunology (2011); 127 (1): 1-55), however, usually the amounts at the lower borders of such immunotherapies are sufficient for the treatment according to the present invention. Accordingly, lipocalin proteins are preferably applied through mucosal surfaces or via the subcutaneous, intramuscular, intranasal, intralymphoidal, etc. route. Systemic (SIT), sublingual immunotherapy (SLIT) and oral immunotherapy (OIT) also being preferred embodiments of the present invention.

According to a preferred embodiment of the present invention the lipocalin proteins are used for treatment at a concentration above 0.1 µg/ml, most preferably 10-100 µg/ml, or up to 600 µg/ml (see e.g. recommendation of WHO; generally higher doses have been regarded as being more effective; according to the present invention, overall reduction of doses can be achieved by the provision of lipocalin holo-allergens). Preferred concentrations of the administered lipocalin proteins are therefore 0.1 to 600 µg/ml, preferably 0.5 to 100 µg/ml, especially 1 to 50 µg/ml. Examples of typical dose regimen of standard allergen immunotherapy are disclosed e.g. in Klimek et al., Clin. Exp. Allergy 42 (2012), 936-945): 20, 40, 80 or 120 µg of total grass pollen recombinant protein. The advantage of the present invention is that due to higher efficacy of siderophore-loaded lipocalins, the doses can be reduced as well as the number of immunization intervals, lowering the risk of side effects. This is an advantageous therapy option in food allergy, which is associated with a high risk today and actually is therefore currently not performed in an efficient manner.

According to the present invention, lipocalin proteins are used in holo-form for specific immunotherapy against allergies.

According to another aspect, the present invention also relates to lipocalin proteins for use in treatment or prevention of autoimmunity diseases, especially celiac disease or inflammatory bowel disease (Crohn's disease, ulcerative colitis). These diseases can be defined as immunological disorders caused by a loss in immunological tolerance resulting in inflammation. Application of immunesuppressive lipocalin proteins in their holo-form might therefore be an attractive tool for immunosuppression and induction of tolerance due to bystander-suppression (Mayer L et al; Nature Rev. Immunol 2004)

According to the present invention, lipocalin proteins are co-applied with siderophores and ligands such as iron or retinoic acid. The formulation is preferably achieved by micro- or nanoparticles entrapping the lipocalin of the invention inside, more preferred, when the microparticles are constituted by poly lacto glycolic acid (PLGA), more preferred when the particle is functionalized by lectins to target immune induction sites, such as wheat germ agglutinin (WGA), most preferred when functionalized with Aleuria aurantia lectin (AAL) which targets alpha-L fucose expressed on M-cells of tonsils and Peyers' patches in the intestine. The particulate formula may be applied with adjuvants such as Montanide, Aluminiumhydroxide, diphtheria or choleratoxin subunits B. The same formula can also be used in a subcutaneous or intramuscular application.

Besides lipocalin proteins, also lipocalin analogues can be used in the treatment according to the present invention. "Lipocalin analogues" according to the present invention include all polypeptides that exert the same allergenic specificity as the naturally occurring lipocalin proteins and have a cavity capable of carrying iron or other ligands typically for lipocalin, such as siderophore-bound iron or retinoic acid. Accordingly, by such definition, lipocalins that do not bind iron efficiently (e.g. via a siderophore) are not to be regarded as "lipocalin analogues" according to the present invention, whereas polypeptides that bind iron (via siderophores) in an efficient manner (as e.g. confirmed by the method according to the present invention), can also be successfully administrated in the therapeutic embodiment of the present invention.

The invention is further disclosed by means of the following examples and the figures.

FIG. 1: Most prominent respiratory allergens are lipocalins. Structural comparison of lipocalins. The crystal structure of human NGAL wild-type protein (1L6M) is shown as a ribbon diagram in cyan with superposed block segments determined with FATCATflex colored in deeper blue. a-c. Single-block superposition with a. bos BLG (3NPO, pink and deep purple), b. dog Can f 1 (model structure, pale green and deep green), and c. Cat Fel d 4 (model structure, white and deep gray) d. Three-blocks, 2-twists superposition with birch Bet v 1 (1BV1, salmon and deeper red hues for the three segments). e. Two-blocks, 1-twist superposition with Alternaria Alt a 1 (3VOR, light orange and yellow and orange for the two segments). f. Scores of FATCATflex, CE, and TM superposition methods used for structural comparisons.

Figure 2:
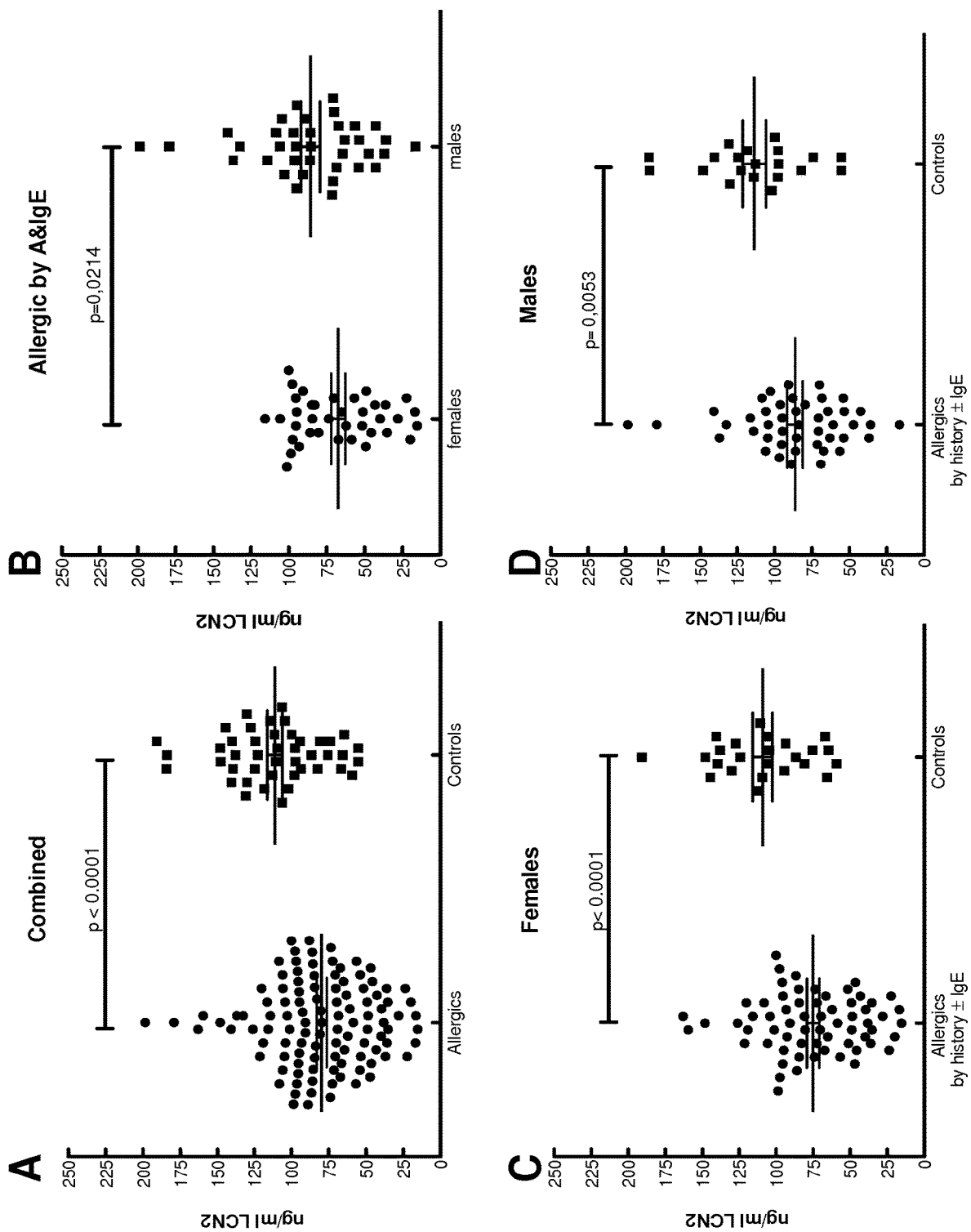

FIG. 2: Allergics have lower LCN2-levels in serum. Serum of healthy and allergic individuals were tested by ELISA for LCN2-levels. In sera of allergic individuals significantly less lipocalin 2 is detected compared to controls (A). In allergics, male individuals had significantly more lipocalin 2 than female subjects in serum (B). Compared to non-allergic controls, lipocalin2-levels in females (C) and males (D) were lower in allergics. All in vitro assays were performed at least twice with highly reproducible data sets. Statistical analyses were conducted with Student's t-test. *$p<0.05$, $p<0.01$, **$p<0.0001$.

FIG. 3: Apo-, but not holo-Lipocalin allergens promote CD4 cell survival. 10000 CD3+ cells of PMA-activated PBMCs incubated with apo- or holo-lipocalin allergens were recorded and analyzed for CD4 and CD8 expression. Representative pictograms of CD3 gated PBMCs stained for CD4 and CD8 as well as summary of CD4 expression (standardized by PMA-control) of individuals tested are depicted, when incubated with a. BLG b. Bet v 1 c. Alt a 1 in the apo and holoform. Statistical analyses were conducted with paired Student's t-test. $p<0.01$, **$p<0.0001$. Data a are from 9 independent experiments with n=26, b from 5 experiments with n=10 and c from 4 experiments with n=7.

Figure 4:
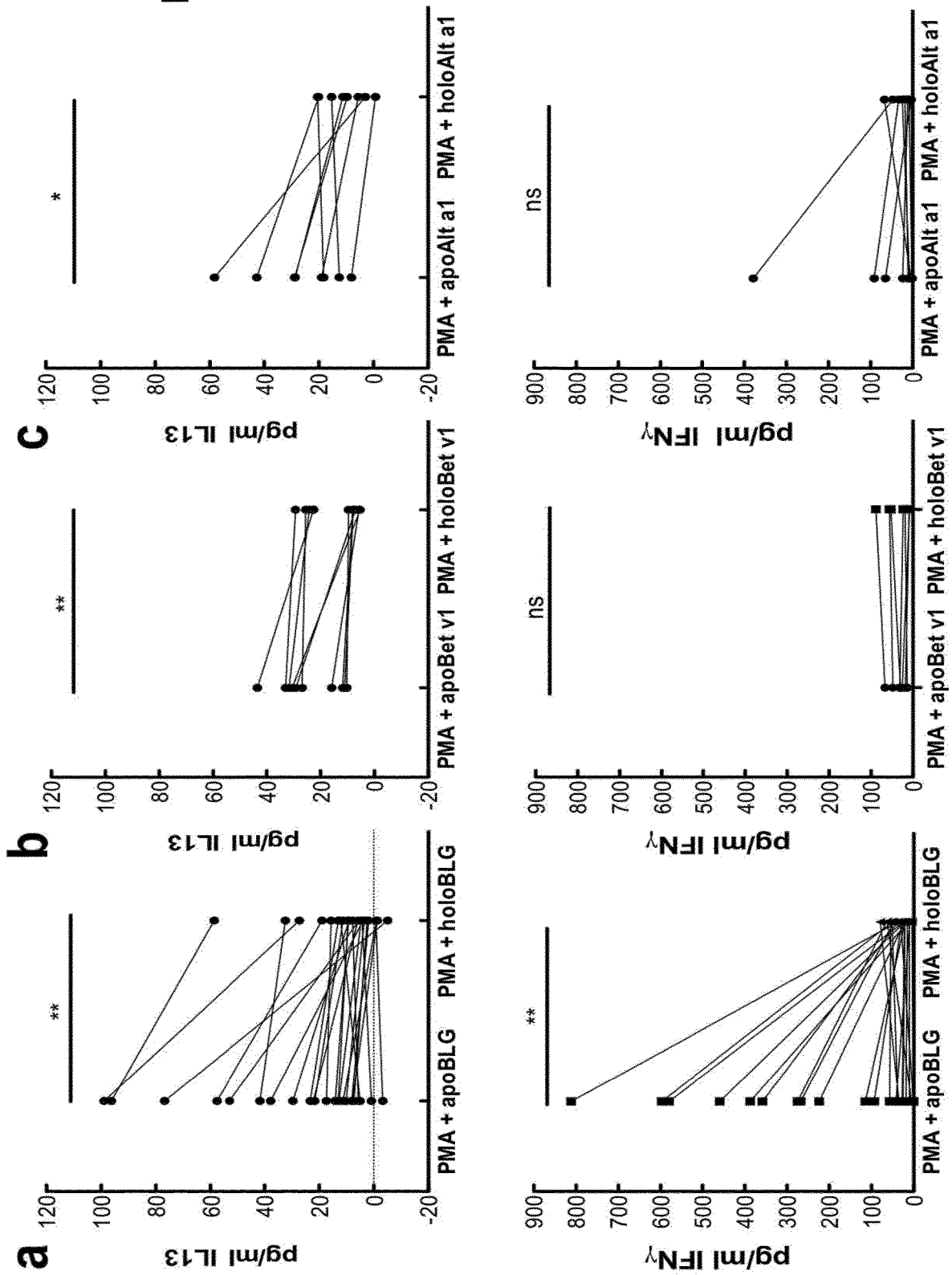

FIG. 4: Th2-cytokines are released upon stimulation with lipocalin allergens in their apo- but not in their holo-form. PMA-activated PBMCs were incubated for 18-24 h with a. apo- and holo-BLG b. apo- and holo-Bet v 1 c. apo- and holo-Alt a 1 and their cytokine-content analyzed for IL13 and IFN-γ. *$p<0.05$, **$p<0.01$, were obtained using paired Student's t-test. Data a are from 9 independent experiments with n=26, b from 5 experiments with n=10 and c from 4 experiments with n=8.

Figure 5:
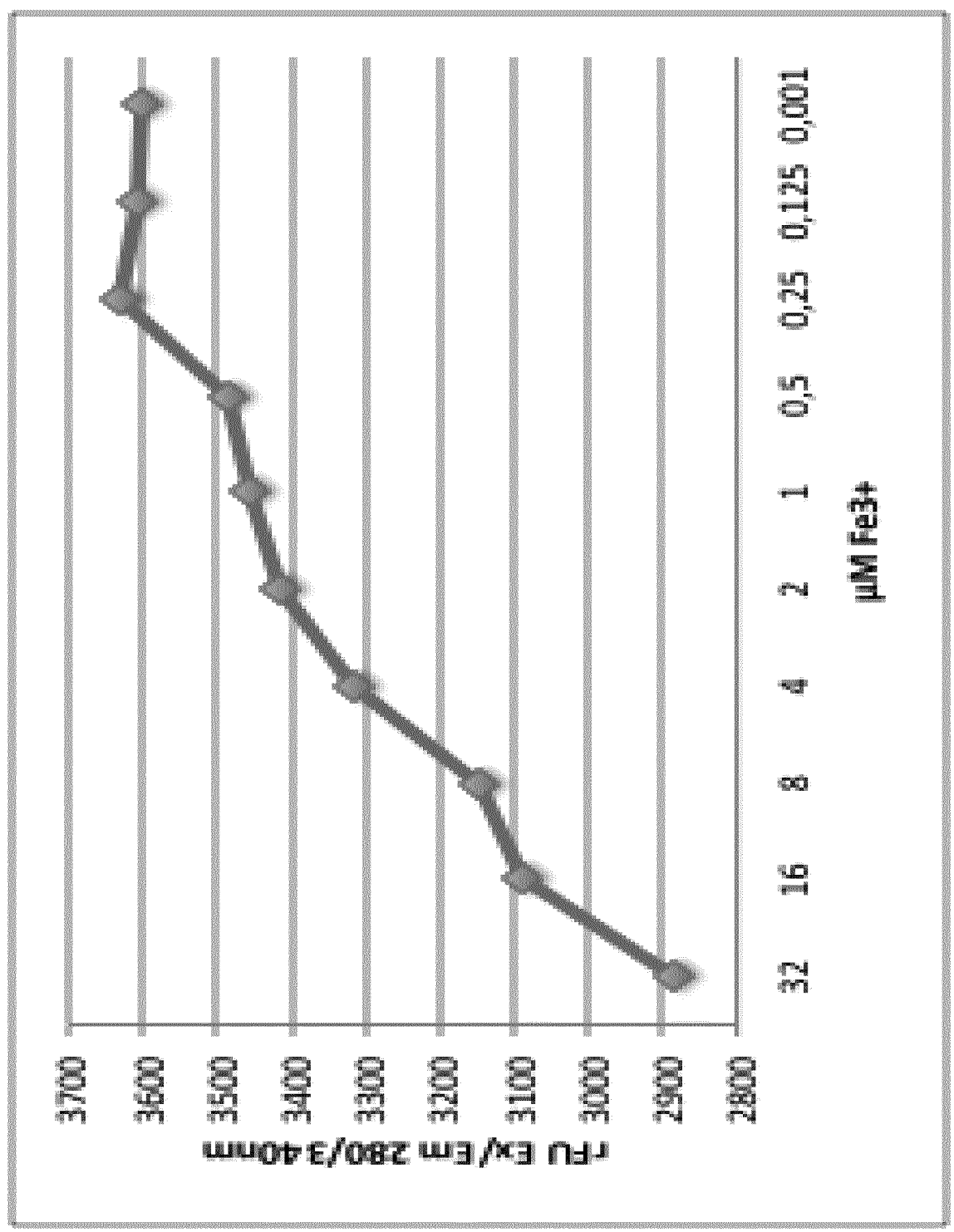

FIG. 5: Iron-binding of BLG. Autofluorescence of the cavity was quenched by addition of siderophore (y-axis) and increasing concentrations of iron (x-axis).

Figures 6A, 6B:
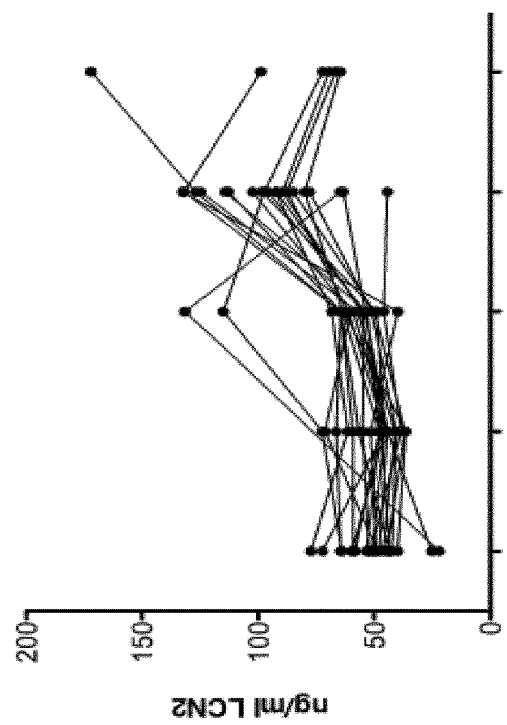

FIG. 6: Serum LCN2 increases after sublingual immunotherapy (SLIT) against grass in allergics. Allergics were randomized and received either placebo (n=10; 6B) or sublingual immunotherapy (n=33; 6A) against grass pollen for 26 weeks. Before (Preslit), within (midslit) and after final SLIT-treatment (post-SLIT) blood samples were taken. Three to six months after termination of SLIT-treatment blood was collected in up to two follow-up visits (post I and post II) and analyzed for serum-LCN2 by ELISA.

EXAMPLES

1. Allergics have Lower LCN2-Levels in Serum than Healthy Controls.

The study according to the present invention was approved by the institutional ethics committee and conducted in accordance with the Helsinki Declaration of 1975. The present study was divided into two parts: for detection of LCN2 in serum a retrospective analysis of prospectively collected samples was conducted, and the second part for isolation of white blood cells. In part one, LCN2 in serum was detected by retrospective analysis. In part two white blood cells were isolated. A total of 143 subjects with suspicion of allergy were tested in an allergy ambulatory for allergen-specific IgE using a microarray-based panel of 112 allergens (ISAC®, Phadia, Sweden) (FIG. 2). Sample size was calculated post hoc ($\alpha$ err 0.05, effect size 0.8) with the power analysis program G*Power 3.1.7 and reached a power of >0.95. Subsequently, LCN2-levels in serum were tested. ELISA plates were coated with rat anti-human Lipocalin 2 (R&D, 2 µg/ml), blocked with 1% BSA/PBS and diluted serum (1:100) or standards were incubated for 3 hours before detecting with biotinylated goat anti-human Lipocalin 2 (100 ng/ml) and Streptavidin-peroxidase (1:200). As substrate TMB was used and stopped after 10 min with 1.8 M sulfuric acid. Absorbance was measured at 450 nm, with a reference wavelength of 630 nm.

Patients were considered lipocalin-allergic (A&IgE) when they suffered from a history of rhinoconjunctivities associated with lipocalin-allergens and had IgE against at least one of following lipocalin-allergens on the microarray: Alt a 1, Bet v 1, Bos d 5, Can f 1 and Can f 2, Der p 2, Der f 2, Equ c1, Fel d 4, Mal d1, Phl p 1 and Phl p 2. Patients with a history of asthma or atopic dermatitis were excluded due to previously reported intrinsic upregulation of LCN2 (n=25). According to published data on age-dependent gender bias in allergic and atopic diseases in humans, we excluded patients under the age of (n=9) and divided the data by gender. All others were considered controls due to unspecific symptoms and history, and negative IgE to lipocalin allergens.

2. Nearly all Major Respiratory and Some Food Allergens Belong to the Lipocalin-Family.
Structural Analysis Three different superposition procedures were employed to compare structure of allergens using (i) FATCAT (Flexible structure AlignmenT by Chaining Aligned Fragment Pairs), which allows flexibility in structurally aligned blocks by introducing a limited number of twists in the superposed structures (Ye et al., Bioinformatics 19 (2003), Suppl 2, ii246), (ii) CE (Combinatorial Extension) algorithm to align structurally fragment pairs (Shindyalov et al., Protein engineering 11 (1998), 739), and (iii) TM (Template Modeling)—align procedure which uses rotation matrices and Dynamic Programming to optimize a structure alignment (Zhang et al., Nucleic acids research 33 (2005), 2302). Both CE and TM methods yield superpositions referring to the protein structure as a whole, whereas FATCATflex superpositions may give two or more superposed structural blocks if one or more twists are introduced (as it is the case here for Bet v 1 and Alt a 1 proteins: see FIG. 1).

For comparisons between crystal structures, FATCATflex and CE superpositions were accomplished by using the j-interface versions of these methods implemented in the PDB Comparison Tool (Prlic et al., Bioinformatics 26 (2010), 2983). For FATCATflex comparisons involving model structures, the FATCAT server and a version compiled for Linux of the CE program were used instead (Ye et al., Nucleic acids research 32 (2004), W582). TM-align superpositions were carried out in all cases using the TM website which allows comparing experimental as well as theoretical structures. Superposed structures with FATCAT-flex p-values <0.05 are considered significantly similar, CE superpositions with z-scores between 3.0 and 4.0 suggest structural similarity, and TM-align superpositions with TM-scores between 0.4 and 0.5 indicate significant structural relationship.

Structures for Can f 1 and Fel d 4 allergens were obtained by homology modeling with SwissModel (Kiefer et al., Nucleic acids research 37 (2009), D387) in automated mode. Can f 1 structure (QMEAN Z-score=+0.503, Evalue=2.34× $10^{-41}$) was modeled based on template 3EYC (60.14% sequence identity) whereas Fel d 4 model structure (QMEAN Z-score=−0.875, Evalue=5.10×$10^{-52}$) was obtained based on template 1EW3 (69.68% sequence identity).

Structural comparisons between NGAL wild-type protein and the allergens BLG, Can f 1, Fel d 4, Bet v 1 and Alt a 1 were studied using the X-ray crystal structures (PDB code in parentheses) for NGAL (1L6M), bos BLG (3NP0), birch Bet v 1 (1BV1), and Alternaria Alt a 1 (3VOR), and the modeled structures for dog Can f 1 and cat Fel d 4.

The results are given in FIG. 1 and show that the selected allergens, against the state of the art, form similar folds in the analysis prompting the conclusion that the lipocalin fold is a significant precondition for allergenicity.

3. Lipocalin Proteins without Binding to Siderophores Cause a Th2-Shift.

In the following experiments it was shown that by pre-activating peripheral blood mononuclear cells, PBMCs, for 24 h with suboptimal concentration of phorbol-12-myristate-13 acetate, PMA (0.75 ng/ml), and addition of apoBLG or apoBetvl (100 µg/m1), an increase in CD4 expression and survival is observed, which was in sharp contrast when same cells were incubated with the holo counterpart containing iron, e.g. holoBLG or holoBetvl (Liu et al., The Journal of Biological Chemistry 2011; 286: 20606-20614). Cells were then stained for CD3-APC, CD8-PE, CD4-PE-CY7, 7AAD and Annexin V-FITC, gated for CD3 and analyzed by a FACS Canto II. Data acquisition was stopped when 10000 CD3 cells were recorded.

The data showed that apo-lipocalins promote survival of activated CD4-cells, whereas holo-lipocalins reduce CD4+ expression on CD3+ cells and promote cell death of CD3+ CD4+ cells. Thus, addition of iron-siderophore to an immunotherapeutic agent significantly modulates a consecutive immune response. This for the first time allows using lipocalin allergens for immunotherapy without causing an undesired Th2-shift.

The advantage of the present invention for immunotherapy is that the use of lipocalins in combination with siderophore-iron-complex in immunotherapy does not cause a Th2-shift and even counterregulate the Th2 bias typical for allergy, thereby abrogating an immune response and thereby leading to a modulation of the immune response to allergens. Moreover, allergen extracts and molecules can be designed according to their apo- or holo-state to redirect the immune response.

4. Lipocalin Proteins for Use in the Treatment of Allergy and Monitoring of Lipocalin 2 (LCN2) Levels to Assess Allergen Immunotherapy Efficacy.

LCN2-levels in serum of an allergic individual were measured before and after 4 months sublingual immunotherapy against horse dander allergy by ELISA. LCN2-levels in serum increased during this time course from 780 ng/ml to 950 ng/ml.

Materials & Methods

General: Commercially available bovine beta-lactoglobulin (Sigma Aldrich, Steinheim, Germany) and recombinant Alternaria alternata (Bial Aristegui, Bilbao, Spain) were prior to use dialyzed first against 10 µM DFO before further dialyzation against deionized water. Recombinant Bet v 1a (Biomay, Vienna, Austria) was used as purchased. The molecular modelling approach and used software is in detail described in the results' section of FIG. 1.

Generation of Holo-Allergens (Examples 3+4)

Apo-allergens were incubated with equimolar concentration of iron (ammonium iron (III) citrate, Sigma) and three-fold molar concentration of catechol, since 3 catechols are necessary for hexadental binding of iron in the LCN2-pocket against deionized water. Recombinant Bet via (Biomay, Vienna, Austria) was used as purchased Isolation of PBMCs (Examples 3+4)

An additional ethical consideration was required for the analysis of blood samples, which was approved by the institutional ethics committee and conducted in accordance with the Helsinki Declaration of 1975. The study was conducted on 30 volunteer blood donors. All subjects gave their full written informed consent, and the study was approved by the Medical University of Vienna ethics committee. Volunteers were divided into two groups (allergics and with no reported allergies) and 15 ml blood were taken.

Blood was mixed with equal volumes of PBS containing 2% FCS before applying onto 10 ml Ficoll-Paque PLUS (GE Healthcare, Uppsala, Sweden), centrifugation at 400 g for 30 min without brake and washing the cells twice with 0.89% sodium chloride solution. Cells were then diluted to a concentration of 1Mio cells/ml in RPMI medium containing 10% FCS. Throughout the study FCS from the same lot was always used.

Stimulation of PBMCs with Allergen (Examples 3+4)

To PBMCs (0.5 Mio/test) a final concentration of 0.75 ng/ml PMA, 100 µg/ml apo-allergen (BLG, Alt a 1 and Bet v 1) with or without 10 µM catechol (Sigma) and 10 µM iron was added. For control purposes each substance was also tested without allergen or PMA. PMA concentration was determined in pre-experiments and considered optimal when cells were slightly downregulating surface CD4+ expression (7). After 18-24 h supernatants were collected and stored at −80° C. until further analysis.

Cells were stained for 30 min at 4° C. with CD3-APC (clone SK7, ebioscience), CD4-PE-Cy7 (clone SK3, BD Bioscience), CD8-PE (clone SK1, BD Bioscience), in PBS containing 2% FCS, followed by 10 min incubation of Annexin V FITC (BD Bioscience) and 7AAD (ebioscience) in Binding buffer (10 mM Hepes, 140 mM NaCl, 2.5 mM CaCl2) at room temperature. Acquisition and analysis was performed on a FACS Canto II machine (BD Bioscience, San Jose, Calif., USA) using the FACSDiva Software 6.0.

Determination of LCN2 and Cytokines (Examples 2+4)

LCN2 and the cytokine levels of IL13 and IFNγ were detected with commercially available kits according to the manufacturers' protocol. Sera were diluted 1:100 before determining LCN2-levels, whereas supernatants of 18-24 h stimulation were used undiluted. Sensitivity of LCN2 assay is about 75 pg/ml and kits were purchased from R&D Systems (Minneapolis, Minn., USA), whereas ELISAs for human IL13 and IFNγ were from ebioscience (Santa Clara, Calif., USA), both assays having a reported sensitivity of 4 pg/ml.

5. Testing of Iron-Binding Capacity of Lipocalin Allergens

In this assay, 2 µM of allergen (in the example BLG) and 50 µM of siderophores like 2,3, Dihydroxybenzoic Acid are incubated with increasing concentrations of iron III (Fe3+) ranging from 0 to 50 µM (x-axis in FIG. 5). Quenching of autofluorescence is measured at excitation and emission wavelengths of 280 and 340 nM respectively in endpoint mode (y-axis in FIG. 5).

6. Serum LCN2 Increases after Sublingual Immunotherapy (SLIT)

LCN2 was detected with commercially available kits according to the manufacturers' protocol. Sera were diluted 1:200 before determining LCN2-levels. LCN2 kits were purchased from R&D Systems (Minneapolis, Minn.). Allergics were randomized and received either placebo (n=10) or sublingual immunotherapy (n=33) against grass pollen for 26 weeks. Before (Preslit), within (midslit) and after final SLIT-treatment (post-SLIT) blood samples were taken. Three to six months after termination of SLIT-treatment blood was collected in up to two follow-up visits (post I and post II) and analyzed for serum-LCN2 by ELISA.

This experiment revealed that serum LCN2 increases after SLIT against grass in allergics (see FIG. 6).

The present invention discloses the following embodiments:

1. A method for diagnosing allergy in a human or animal patient, wherein the level of species-specific lipocalin, especially lipocalin 2 in a human patient, is measured in a sample of said patient and wherein a lowered level of said lipocalin compared to the level of said lipocalin in the corresponding sample of a human or animal that has no allergy, is indicative of an allergy.

2. Method according to embodiment 1, wherein the sample is a body fluid, preferably a blood, serum, plasma, urine, saliva, tear fluid, lymph, or mucosa sample, a dander sample, or a hair sample.

3. Method according to embodiment 2, wherein the body fluid is blood, serum or plasma and the patient is a human patient or veterinarian patient, preferably dog, cat, or horse.

4. Method according to any one of embodiments 1 to 3, wherein the level of species-specific lipocalin, especially lipocalin 2, is lowered by at least 5% with respect to the ng lipocalin 2/ml body fluid, preferably by at least 10%, especially at least 15%, compared to the level of species-specific lipocalin, especially lipocalin 2, in the corresponding sample of a human or animal that has no allergy, said corresponding sample having no allergy defining the 100% level.

5. Method according to any one of embodiments 1 to 4, wherein the level of species-specific lipocalin, especially lipocalin 2, is measured by immunological techniques, especially by ELISA, ELISPOT, immunoblot, or other immunological solid phase assays; or by measuring the level of species-specific lipocalin mRNA, especially lipocalin 2 mRNA, in the sample, preferably by PCR, especially real time PCR.

6. Kit for performing a method according to any one of embodiments 1 to 5, comprising means for detecting the level of a species-specific lipocalin, especially lipocalin 2, especially a molecule binding to the species-specific lipocalin, especially lipocalin 2, and means for comparing the level of the species-specific lipocalin, especially lipocalin 2, to be detected with the level of the species-specific lipocalin, especially lipocalin 2, in a human or animal that has no allergy.

7. Kit according to embodiment 6, wherein the means for detecting the level of species-specific lipocalin, especially lipocalin 2, is an anti-species-specific lipocalin antibody, preferably an anti-lipocalin 2 antibody or a lipocalin 2-binding antibody fragment, especially an anti-human lipocalin 2 antibody or a human lipocalin 2-binding antibody fragment.

8. Kit according to embodiment 6 or 7, further comprising a marker, preferably a colourigenic, fluorescent, luminescent, magnetic or radioactive marker, especially a marker that is covalently linked to the means for detecting the level of a species-specific lipocalin, especially lipocalin 2, or a marker that is covalently linked to the molecule binding to a species-specific lipocalin, especially lipocalin 2.

9. Kit according to any one of embodiments 6 to 8, further comprising one or more standards for a species-specific lipocalin, especially lipocalin 2.

10. Method for determining the quantity of unloaded lipocalin 2 in a lipocalin 2 containing preparation wherein
(a) a predetermined amount of test siderophore is added to the preparation or
(b) the preparation is competitively tested with iron-ligands not able to bind to the lipocalin cavity, preferably desferral, that extracts ligands from the lipocalin-pocket resulting in the reestablishment of the intrinsic fluorescence of the proteins; or
(c) fluorescent, chromogenic, radiolabelled siderophore-iron-complexes are used directly or competitively for binding to the lipocalin cavity
and wherein the quantity of unloaded lipocalin 2 is determined by (a) quenching of the autofluorescence of lipocalin proteins (b) autofluorescence of lipocalin proteins, or (c) measurement of bound siderophore.

11. Lipocalin proteins for use in treatment or prevention of allergies, wherein the lipocalin proteins are provided together with a siderophore and a metal ion, especially an iron ion, in their holo-form.

12. Lipocalin proteins according to embodiment 11, wherein the treatment is a reduction and amelioration of allergy symptoms 13. Lipocalin proteins according to embodiments 11 or 12, wherein the lipocalin proteins are administered in combination with metal-ions, preferably Fe, Cu, Zn, Se or Mn, especially iron $Fe^{3+}$.

14. Lipocalin proteins according to any one of embodiments 11 to 13, wherein lipocalin proteins are administered together with a metal-ion, preferably iron complexed with siderophores, in a molar ratio of 0.5 to 3 to 3 to 0.5, preferably in a molar ratio of 1 to 3 to 3 to 1, especially in a molar ratio of 2.0 to 3 to 3 to 2.

15. Lipocalin proteins according to any one of embodiments 11 to 14, wherein lipocalin proteins are administered with zinc-, copper-, selen-, or mangan-ions.

16. Lipocalin proteins according to any one of embodiments 11 to 15, wherein lipocalin proteins are administered with siderophores selected from catechols or catechol-derivatives comprising 2 hydroxygroups in ortho position.

17. Lipocalin proteins according to any one of embodiments 11 to 15, wherein lipocalin proteins are administered with siderophores selected from the hydroxamate and hydroxypyridinone ligand families as well as of carboxylate and its derivates where in the α-position a hydroxy- or amino-group is present.

17. Lipocalin proteins according to any one of embodiments 11 to 16, wherein lipocalin proteins are selected from human lipocalin 2, Amb a 1, Aln g 1, Aca s 13, Act c 8, Act d 8, Act d 11, Alt a 1, Asp f 1, Asp f 3, Asp f 6, Art v 1, Api g 1, Api m1, Act d 2, Act d 8, Ara h 8, Arg r 1, Ber e 1, Bet v 1, Bet ch 1, Bet co 1, Bet le 1, Bet n 1, Bet p 1, Blo t5, Bla g 1, Bla g 4, Bos d 2, Bos d 5, Bub b BLG, Can f 1, Canf 2, Can f 6, Cap h BLG, Car b 1, Cas s 1, Cav p 1, Cav p 2, Cav p 3, Cla h 8, Cyn d 1, Cyn d 2, Cyn d 15, Cor a 1, Cor he 1, Che a 1, Cup a 1, Dac g 1, Dac g 2, Dac g 3, Dau c 1, Der p 2, Der f 2, Der f 13, Der p 13, Ecqu c 1, Ecqu c 2, Fag s 1, Fra a 1, Fel d 4, Fel d 7, Gly m 4, Hol l 1, Hom s TL, Hey b 8, Jug r 2, Lep d 13, Lol p 1, Lol p 2, Lol p3, Lyc e 4, Mal d 1, Mer a 1, Mus m 1, Ole e 1, Ory c 1, Ory s 1, Ost c 1, Ovi a BLG, Pas n 1, Pha a 1, Per a 4, Pru ar 1, Pru av 1, Pru p 1, Phl p 1, Phl p 2, Phl p 3, Phl p 11, Pla a 2, Poa p 1, Poa p2, Que a 1, Rant t BLG, Rat n 1, Rub I 1, Sal k 1, Sus s 1, In a 1, In a 2, Tria p 1, Tyr p 13, Ves v 5, Vig r 1, Zea m 1, Zea m3 and lipocalins of insects, ticks, spiders and fungi.

18. Lipocalin proteins according to any one of embodiments 11 to 17, wherein lipocalin proteins are applied in a systemic immunotherapy, sublingual immunotherapy or oral immunotherapy.

19. Lipocalin proteins according to any one of embodiments 11 to 18, wherein lipocalin proteins are applied intramuscularly, intranasally, or intralymphatically.

20. Lipocalin proteins according to any one of embodiments 11 to 19, wherein lipocalin proteins are applied through mucosal surfaces or via the subcutaneous route.

21. Lipocalin proteins according to any one of embodiments 11 to 20, wherein lipocalin proteins are used at a concentration of 0.1 to 600 µg/ml, preferably of 0.5 to 100 µg/ml, especially 1 to 50 10 µg/ml.

The invention claimed is:

1. A method of treating allergies, which comprises administering to a patient in need thereof, a therapeutically effective amount of at least one protein selected from human lipocalin 2, Alt a 1, Bet v 1, BLG, Can f 1, and Fel d 4, wherein the protein is provided together with a catechol, a catechol-derivative, and/or retinoic acid, and a metal ion selected from Fe and/or Zn.

2. The method according to claim 1, which comprises a reduction and amelioration of allergy symptoms.

3. The method according to claim 1, wherein the protein is administered in combination with Fe.

4. The method according to claim 1, wherein the protein is administered together with a metal-ion complexed with a catechol, a catechol-derivative and/or retinoic acid, in a molar ratio of 0.5 to 3 to 3 to 0.5.

5. The method according to claim 1, wherein the protein is administered using systemic immunotherapy, sublingual immunotherapy or oral immunotherapy.

6. The method according to claim 1, wherein the protein is administered intramuscularly, intranasally, intralymphatically or through mucosal surfaces or via the subcutaneous route.

7. The method according to claim 1, wherein the protein is administered at a concentration of 0.1 to 600 µg/ml.

8. The method according to claim 1, wherein the protein is administered together with a metal-ion complexed with a catechol, a catechol-derivative and/or retinoic acid, in a molar ratio of 1 to 3 to 3 to 1.

9. The method according to claim 1, wherein the protein is administered together with a metal-ion complexed with a catechol, a catechol-derivative and/or retinoic acid, in a molar ratio of 2.0 to 3 to 3 to 2.

10. The method according to claim 1, wherein the protein is administered at a concentration of 0.5 to 100 µg/ml.

11. The method according to claim 1, wherein the protein is administered at a concentration of 1 to 50 µg/ml.

12. A method of treating allergies, which comprises administering to a patient in need thereof, a therapeutically effective amount of BLG provided together with a catechol, a catechol-derivative, and/or retinoic acid, and a metal ion selected from Fe and/or Zn.

* * * * *